(12) United States Patent
Adler

(10) Patent No.: US 7,758,499 B2
(45) Date of Patent: Jul. 20, 2010

(54) METHOD AND APPARATUS FOR VIEWING THROUGH BLOOD

(75) Inventor: Doron Adler, Nesher (IL)

(73) Assignee: C2Cure, Inc., Wilmington, DE (US)

( * ) Notice: Subject to any disclaimer, the term of this patent is extended or adjusted under 35 U.S.C. 154(b) by 791 days.

(21) Appl. No.: 11/560,796

(22) Filed: Nov. 16, 2006

(65) Prior Publication Data

US 2007/0100241 A1 May 3, 2007

Related U.S. Application Data

(62) Division of application No. 10/759,045, filed on Jan. 20, 2004, now abandoned, which is a division of application No. 09/973,181, filed on Oct. 10, 2001, now Pat. No. 6,692,430.

(60) Provisional application No. 60/311,093, filed on Aug. 10, 2001.

(51) Int. Cl.
*A61B 1/015* (2006.01)
*A61B 1/05* (2006.01)
(52) U.S. Cl. .................. 600/158; 600/109; 600/156
(58) Field of Classification Search .................. 600/109, 600/153, 156, 158
See application file for complete search history.

(56) References Cited

U.S. PATENT DOCUMENTS

| 3,321,656 | A | 5/1967 | Sheldon |
| 3,971,065 | A | 7/1976 | Bayer |
| 4,253,447 | A | 3/1981 | Moore et al. |
| 4,261,344 | A | 4/1981 | Moore et al. |
| 4,448,188 | A * | 5/1984 | Loeb ..................... 600/108 |
| 4,467,361 | A | 8/1984 | Ohno et al. |
| 4,491,865 | A | 1/1985 | Danna et al. |
| 4,555,768 | A | 11/1985 | Lewis, Jr. et al. |
| 4,569,335 | A | 2/1986 | Tsuno |
| 4,573,450 | A | 3/1986 | Arakawa |
| 4,576,146 | A | 3/1986 | Kawazoe et al. |
| 4,602,281 | A * | 7/1986 | Nagasaki et al. ............. 348/69 |
| 4,604,992 | A | 8/1986 | Sato |

(Continued)

FOREIGN PATENT DOCUMENTS

CA 2173113 A1 4/1995

(Continued)

OTHER PUBLICATIONS

European Examination Report for related European patent application No. 01919745.8, dated Nov. 28, 2007, 2 pages.

(Continued)

*Primary Examiner*—John P Leubecker
(74) *Attorney, Agent, or Firm*—Ganz Law, P.C.

(57) ABSTRACT

A method, apparatus, and system for viewing through blood in situ including a flexible catheter for insertion into a blood vessel, an optical assembly positioned at the distal end of the catheter, a working channel, and a control unit for regulating the opacity level of blood in the blood vessel around the distal end of the catheter and controllably injecting quantities of fluid into the blood vessel in the vicinity of the optical assembly. A local controller located at the distal end of the catheter may control functions of the optical assembly while coordinating signals and power with the control unit. Some possible embodiments, may include an inflatable stent balloon.

11 Claims, 9 Drawing Sheets

U.S. PATENT DOCUMENTS

| | | | |
|---|---|---|---|
| 4,611,888 A * | 9/1986 | Prenovitz et al. | 600/112 |
| 4,625,236 A | 11/1986 | Fujimori et al. | |
| 4,633,304 A | 12/1986 | Nagasaki | |
| 4,646,721 A | 3/1987 | Arakawa | |
| 4,651,201 A | 3/1987 | Schoolman | |
| 4,682,219 A | 7/1987 | Arakawa et al. | |
| 4,692,608 A | 9/1987 | Cooper et al. | |
| 4,697,208 A | 9/1987 | Eino | |
| 4,713,683 A | 12/1987 | Fujimori et al. | |
| 4,714,319 A | 12/1987 | Zeevi et al. | |
| 4,720,178 A | 1/1988 | Nishioka et al. | |
| 4,739,766 A * | 4/1988 | Riederer | 600/413 |
| 4,746,203 A | 5/1988 | Nishioka et al. | |
| 4,757,805 A | 7/1988 | Yabe | |
| 4,768,513 A | 9/1988 | Suzuki | |
| 4,784,133 A | 11/1988 | Mackin | |
| 4,803,550 A | 2/1989 | Yabe et al. | |
| 4,803,562 A | 2/1989 | Eino | |
| 4,809,680 A | 3/1989 | Yabe | |
| 4,819,065 A | 4/1989 | Eino | |
| 4,827,907 A | 5/1989 | Tashiro | |
| 4,831,456 A | 5/1989 | Takamura et al. | |
| 4,832,003 A | 5/1989 | Yabe | |
| 4,832,033 A | 5/1989 | Maher et al. | |
| 4,857,724 A | 8/1989 | Snoeren | |
| 4,866,526 A | 9/1989 | Ams et al. | |
| 4,869,256 A | 9/1989 | Kanno et al. | |
| 4,884,133 A | 11/1989 | Kanno et al. | |
| 4,905,670 A | 3/1990 | Adair | |
| 4,926,257 A | 5/1990 | Miyazaki | |
| 4,934,339 A | 6/1990 | Kato | |
| 4,939,573 A | 7/1990 | Teranishi et al. | |
| 4,953,539 A | 9/1990 | Nakamura et al. | |
| 4,967,269 A | 10/1990 | Sasagawa et al. | |
| 4,986,642 A | 1/1991 | Yokota et al. | |
| 4,998,972 A | 3/1991 | Chin et al. | |
| 5,010,875 A | 4/1991 | Kato | |
| 5,021,888 A | 6/1991 | Kondou et al. | |
| 5,022,399 A | 6/1991 | Biegeleisen | |
| 5,029,574 A | 7/1991 | Shimamura et al. | |
| 5,122,650 A | 6/1992 | McKinley | |
| 5,166,787 A | 11/1992 | Irion | |
| 5,184,223 A | 2/1993 | Mihara | |
| 5,191,203 A | 3/1993 | McKinley | |
| 5,216,512 A | 6/1993 | Bruijns et al. | |
| 5,222,477 A | 6/1993 | Lia | |
| 5,264,925 A | 11/1993 | Shipp et al. | |
| 5,301,090 A | 4/1994 | Hed | |
| 5,311,600 A | 5/1994 | Aghajan et al. | |
| 5,323,233 A | 6/1994 | Yamagami et al. | |
| 5,325,847 A | 7/1994 | Matsuno | |
| 5,335,662 A | 8/1994 | Kimura et al. | |
| 5,343,254 A | 8/1994 | Wada et al. | |
| 5,376,960 A | 12/1994 | Wurster | |
| 5,408,268 A | 4/1995 | Shipp | |
| 5,432,543 A | 7/1995 | Hasegawa et al. | |
| 5,444,574 A | 8/1995 | Ono et al. | |
| 5,450,243 A | 9/1995 | Nishioka | |
| 5,471,237 A | 11/1995 | Shipp | |
| 5,494,483 A | 2/1996 | Adair | |
| 5,498,230 A | 3/1996 | Adair | |
| 5,512,940 A | 4/1996 | Takasugi et al. | |
| 5,547,455 A | 8/1996 | McKenna et al. | |
| 5,557,324 A | 9/1996 | Wolff | |
| 5,575,754 A | 11/1996 | Konomura | |
| 5,594,497 A | 1/1997 | Ahern et al. | |
| 5,598,205 A | 1/1997 | Nishioka | |
| 5,603,687 A | 2/1997 | Hori et al. | |
| 5,668,596 A | 9/1997 | Vogel | |
| 5,673,147 A | 9/1997 | McKinley | |
| 5,700,236 A | 12/1997 | Sauer et al. | |
| 5,712,493 A | 1/1998 | Mori et al. | |
| 5,728,044 A | 3/1998 | Shan | |
| 5,751,341 A | 5/1998 | Chaleki et al. | |
| 5,792,045 A | 8/1998 | Adair | |
| 5,797,837 A | 8/1998 | Minami | |
| 5,847,394 A | 12/1998 | Alfano et al. | |
| 5,905,597 A | 5/1999 | Mizouchi et al. | |
| 5,907,178 A | 5/1999 | Baker et al. | |
| 5,928,137 A | 7/1999 | Green | |
| 5,929,901 A | 7/1999 | Adair et al. | |
| 5,940,126 A | 8/1999 | Kimura | |
| 5,944,655 A | 8/1999 | Becker | |
| 5,984,860 A | 11/1999 | Shan | |
| 5,986,693 A | 11/1999 | Adair et al. | |
| 6,001,084 A | 12/1999 | Riek et al. | |
| 6,009,189 A | 12/1999 | Schaack | |
| 6,010,449 A | 1/2000 | Selmon et al. | |
| 6,039,693 A | 3/2000 | Seward et al. | |
| 6,043,839 A | 3/2000 | Adair et al. | |
| 6,075,235 A | 6/2000 | Chun | |
| 6,099,475 A | 8/2000 | Seward et al. | |
| 6,129,672 A | 10/2000 | Seward et al. | |
| 6,134,003 A | 10/2000 | Tearney et al. | |
| 6,139,490 A | 10/2000 | Breidenthal et al. | |
| 6,142,930 A | 11/2000 | Ito et al. | |
| 6,148,227 A | 11/2000 | Wagnieres et al. | |
| 6,177,984 B1 | 1/2001 | Jacques | |
| 6,178,346 B1 | 1/2001 | Amundson et al. | |
| 6,184,923 B1 | 2/2001 | Miyazaki | |
| 6,206,825 B1 | 3/2001 | Tsuyuki | |
| 6,240,312 B1 | 5/2001 | Alfano et al. | |
| 6,281,506 B1 | 8/2001 | Fujita et al. | |
| 6,315,712 B1 * | 11/2001 | Rovegno | 600/109 |
| 6,327,374 B1 | 12/2001 | Piironen et al. | |
| 6,331,156 B1 | 12/2001 | Haefele et al. | |
| 6,416,463 B1 | 7/2002 | Tsuzuki et al. | |
| 6,449,006 B1 | 9/2002 | Shipp | |
| 6,459,919 B1 | 10/2002 | Lys et al. | |
| 6,464,633 B1 | 10/2002 | Hosoda et al. | |
| 6,476,851 B1 | 11/2002 | Nakamura | |
| 6,477,479 B1 | 11/2002 | Mansky et al. | |
| 6,485,414 B1 | 11/2002 | Neuberger | |
| 6,533,722 B2 | 3/2003 | Nakashima | |
| 6,659,940 B2 | 12/2003 | Adler | |
| 6,670,636 B2 | 12/2003 | Hayashi et al. | |
| 6,692,430 B2 | 2/2004 | Adler | |
| 6,697,110 B1 | 2/2004 | Jaspers et al. | |
| 6,927,791 B2 | 8/2005 | Kole | |
| 6,943,837 B1 | 9/2005 | Booth, Jr. | |
| 6,984,205 B2 | 1/2006 | Gazdzinski | |
| 7,106,910 B2 | 9/2006 | Acharya et al. | |
| 7,123,301 B1 | 10/2006 | Nakamura et al. | |
| 7,127,280 B2 | 10/2006 | Dauga | |
| 7,133,073 B1 | 11/2006 | Neter | |
| 7,308,296 B2 | 12/2007 | Lys et al. | |
| 7,347,817 B2 | 3/2008 | Glukhovsky et al. | |
| 7,355,625 B1 | 4/2008 | Mochida et al. | |
| 2001/0031912 A1 | 10/2001 | Adler | |
| 2001/0040211 A1 | 11/2001 | Nagaoka | |
| 2001/0051766 A1 | 12/2001 | Gazdzinski | |
| 2002/0089586 A1 | 7/2002 | Suzuki et al. | |
| 2003/0174409 A1 | 9/2003 | Nagaoka | |
| 2004/0019255 A1 | 1/2004 | Sakiyama | |
| 2005/0168602 A1 | 8/2005 | Sumi et al. | |
| 2005/0259487 A1 | 11/2005 | Glukhovsky et al. | |
| 2006/0087572 A1 | 4/2006 | Schroeder | |
| 2006/0158512 A1 | 7/2006 | Iddan et al. | |

FOREIGN PATENT DOCUMENTS

| | | |
|---|---|---|
| DE | 3529026 | 2/1986 |
| DE | 3720624 | 1/1989 |
| DE | 19800312 | 7/1999 |

| | | | |
|---|---|---|---|
| EP | 0630056 | | 5/1994 |
| EP | 434793 | B1 | 4/1995 |
| EP | 0827908 | A1 | 3/1998 |
| JP | 61018915 | A | 7/1984 |
| JP | 60258515 | | 5/1985 |
| JP | 63244011 | A | 3/1987 |
| JP | 64-068412 | | 3/1989 |
| JP | 01-238853 | | 9/1989 |
| JP | 02-177965 | | 7/1990 |
| JP | 4236934 | A | 1/1991 |
| JP | 3264043 | A | 11/1991 |
| JP | 04329922 | | 11/1992 |
| JP | 5307144 | | 11/1993 |
| JP | 06222283 | A2 | 12/1993 |
| JP | 7163517 | A | 12/1993 |
| JP | 8220448 | A | 2/1995 |
| JP | 7318815 | A | 6/1995 |
| JP | 8024219 | A | 1/1996 |
| JP | 08082751 | A | 3/1996 |
| JP | 8114755 | A | 5/1996 |
| JP | 10-127564 | | 5/1998 |
| JP | 11019026 | | 1/1999 |
| JP | 11-056757 | | 3/1999 |
| JP | 2000232981 | | 8/2000 |
| JP | 2001-095751 | | 4/2001 |
| JP | 2001-178675 | | 7/2001 |
| JP | 2006198424 | | 3/2006 |
| WO | WO9715229 | A1 | 5/1997 |
| WO | WO9732534 | A1 | 9/1997 |
| WO | WO99/23812 | A2 | 11/1998 |
| WO | WO9960916 | | 2/1999 |
| WO | WO0045691 | | 8/2000 |
| WO | WO0122741 | A2 | 3/2001 |
| WO | WO/01/76452 | | 10/2001 |
| WO | WO03013624 | A2 | 2/2003 |
| WO | WO03/098913 | A3 | 5/2003 |

OTHER PUBLICATIONS

Office Action dated Dec. 1, 2008 for related Israel Patent Application No. 162420 (in the Hebrew language); 3 pages.
Office Action for co-pending Application No. 11/298,265, dated Apr. 2, 2008.
European Examination Report for European Application No. 01919745.8, dated Jul. 20, 2006, EPO, 4 pages.
PCT International Search Report dated Oct. 21, 2001, for corresponding PCT International Application No. PCT/IL01/00313, filed Apr. 4, 2001, 3 pages.
PCT International Search Report dated Jul. 9, 2004, for corresponding PCT International Application No. PCT/US03/32975, filed Oct. 17, 2003.
PCT International Search Report dated Jun. 4, 2003, for corresponding PCT International Application No. PCT/IL02/00999, filed Dec. 11, 2002.
PCT International Search Report dated Mar. 24, 2004, for corresponding PCT International Application No. PCT/IL03/00399, filed May 15, 2003.
United States Patent and Trademark Office Action dated Aug. 9, 2006 for U.S. Appl. No. 10/759,045, filed Jan. 20, 2004, 9 pages.
"A Review of the optical Properties of Biological Tissues," Cheong, Prahl and Welch, IEEE Journal of Quantum Electronics, vol. 26, Dec. 12, 1990.
"Optical Properties of Circulating Human Blood in Wavelength Range 400-2500 nm," Andre Rosgan, Journal of Biomedical Optics, Jan. 1999.
Fujipoly America Corp—Zebra Elastomeric Connectors, http://www.fujipoly.com/products/genProductLine.asp?Productline=zebra; accessed Jun. 11, 2004.
Unpublished U.S. Appl. No. 10/759,045 filed Jan. 20, 2004.
International Search Report dated Jun. 30, 2004 for related International patent application No. PCTIL0200659, filed Aug. 11, 2002; 1 page.
European Search Report dated Nov. 26, 2008 for related European patent application No. EP02758761, filed Aug. 11, 2002; 6 pages.
Mizuno, K. et al. "New Percutaneous Transluminal Coronary Angioscope" Selected papers on optical fibers in Medicine; SPIE Milestone Series; Bellingham, SPIE, US, vol. MS 11, Jan. 1, 1990 pp. 150-155.
Examination Report for related European patent application No. 01919745.8, dated Nov. 28, 2007, EPO cites DE19800312, 2 pgs.
Supplementary European Search Report dated Dec. 22, 2008 for related European patent application No. 02795407.2; 4 pages.
Office action for related Japanese patent application 2003-518624 5 pages.
Office Action from the Patent Office of Canada dated Dec. 29, 2009 for a related Canadian patent application No. 2,456,418, 6 pages.

* cited by examiner

METHOD AND APPARATUS FOR VIEWING THROUGH BLOOD

RELATED APPLICATIONS

The present application is a divisional of U.S. patent application Ser. No. 10/759,045 filed Jan. 20, 2004, which is a divisional of U.S. patent application Ser. No. 09/973,181 filed Oct. 10, 2001, now U.S. Pat. No. 6,692,430, issued Feb. 17, 2004, which claims priority to and the benefit of U.S. Provisional Patent Application No. 60/311,093 filed Aug. 10, 2001, the contents of which are each hereby incorporated by reference as if included in their entirety for all purposes.

The application is also related to U.S. patent application Ser. No. 09/826,163, filed Apr. 5, 2001 now U.S. Pat. No. 6,659,940, issued Dec. 9, 2003, which claims priority from Israel Patent Application No. 135571, filed Apr. 10, 2000, the contents of which are hereby incorporated by reference.

BACKGROUND

The present invention relates to an intra-vascular imaging method and apparatus which allow the acquisition of endoscopic images of small internal cavities of the body including methods and apparatus for visualization through opaque liquid media.

Heart and blood vessel diseases are among the main causes for morbidity and mortality in Western society. Therefore, interventional procedures involving blood vessels of the heart are among the most widely used in the medical field. The pathology that is in the base of most acute coronary syndromes and sudden cardiac deaths is atherosclerosis. In this process, atherosclerotic plaques, which are an active collection of different cells, mainly immune cells and smooth muscle cells along with deposits of fatty substances, cholesterol, cellular waste products, calcium and other substances, are accumulated in the inner lining of an artery. Stable plaques, which cause the more significant narrowing of the arterial wall, are considered the major factor in the development of angina pectoris (chest pain). However, studies from recent years have shown, that unstable angina, myocardial infarctions (heart attacks) and sudden cardiac related deaths are caused mainly by unstable plaques, otherwise known as vulnerable plaques. This type of plaque is usually smaller and therefore less significant and difficult to detect with currently used angiographic methods described hereafter.

Some of the important developments were made in the field of minimally invasive procedures. A very common diagnostic and therapeutic procedure is cardiac catheterization. The commonly applied method, angiography, includes imaging the heart and coronary blood vessels using an X-ray camera as the imaging device, and a catheter, through which a contrast substance is injected into the heart and vessels to enable them to be viewed by the camera. This method gives a two-dimensional monochromatic view of the heart and blood vessels as viewed from the outside. This method detects major occlusions by identifying places where blood flow is disturbed and it may direct the PTCA (Percutaneous Transluminal Coronary Angioplasty) or stent-inserting technique to the place of the occlusion, but it does not give a direct view of the occlusion site or the surrounding area. One of the major risks of the techniques described above is a rupture or a disruption in the fibrous cap covering the plaque and the release of plaque particles into the blood stream. These particles may cause numerous small occlusions in the coronary arteries but also may cause occlusions in small blood vessels of other organs, such as the brain, kidney, or lungs. A direct, clear view of the field of operation, as provided in the current invention, could substantially decrease the risk of disruption, as described above. Also, and perhaps more importantly, only through intra-vascular imaging will it be possible to detect the smaller, vulnerable plaques. The effectiveness and precision of the plaque treatment, when assisted with direct intra-vascular imaging, such as in the present invention, would be enhanced when compared to current indirect imaging methods.

Important methods that have been developed to confront the issue of intra-vascular imaging are angioscopy and intraluminal ultrasound. New techniques, which are still under development, include Optical Coherence Tomography (OCT) and infrared endoscopy.

Angioscopy is a form of endoscopy developed for the arteries. Because the illumination used in angioscopy is in the visible wavelength range, in which the blood that fills the arteries is opaque, the method requires a way of moving the blood from the field of view prior to visualization. One way to do this is by injecting a high-pressure physiological fluid into the vessel to temporarily displace the blood, as disclosed in U.S. Pat. No. 4,827,907, U.S. Pat. No. 4,998,972, U.S. Pat. No. 5,730,731, U.S. Pat. No. 5,010,875 and U.S. Pat. No. 4,934,339. Another way of clearing the field of view is by inflating a balloon, which is positioned at the distal end of the angioscope, in front of the camera-head or optical assembly. The balloon is made of a transparent substance, so that when it is inflated inside the blood vessel, with either gas or a transparent liquid, it pushes the blood away from the distal end of the angioscope and clears a field of view of the walls of the vessel. Such an apparatus is described in U.S. Pat. No. 4,784,133 and U.S. Pat. No. 5,411,016; the latter patent disclosing a transparent part at the distal end of the angioscope in addition to the balloon surrounding it. A similar apparatus is disclosed in U.S. Pat. No. 4,470,407, except that the optical system terminates inside the balloon (also allowing laser operation through the balloon). An apparatus that uses two spaced and expendable balloons, that occlude and isolate an operating area in the blood vessel between them, is disclosed in U.S. Pat. No. 4,445,892. Most methods combine an inflatable balloon with injection of a transparent liquid. The balloon coaxially surrounds the sheath at the distal end of the catheter and, when inflated, it blocks some of the blood flow. The method described above allows the injection of less flush liquid and at a lower pressure, which is safer and more efficient. Prior art in which the method described above is used in U.S. Pat. No. 4,576,145, U.S. Pat. No. 4,576,146, U.S. Pat. No. 5,263,928 and U.S. Pat. No. 5,464,394. A combination of an angioplasty balloon with intra-vascular endoscopy is disclosed in patents EP177124A, U.S. Pat. No. 5,116,317 and U.S. Pat. No. 4,961,738. In the latter patent, the optical system terminates within the balloon and there is a "working well" in the balloon to allow the insertion of instruments into the lumen of the vessel.

Another method for intra-vascular imaging is the use of ultrasound. The ultrasound transducer is positioned at the distal end of a catheter inside the blood vessel and the ultrasound transducer is used to obtain an image of the lumen and walls of the artery. Patents referring to this kind of apparatus are U.S. Pat. No. 6,129,672, U.S. Pat. No. 6,099,475, U.S. Pat. No. 6,039,693, U.S. Pat. No. 6,059,731, U.S. Pat. No. 5,022,399, U.S. Pat. No. 4,587,972, U.S. Pat. No. 4,794,931, U.S. Pat. No. 4,917,097 and U.S. Pat. No. 5,486,170. A patent that combines PTCA with ultrasonic imaging is U.S. Pat. No. 5,167,233.

OCT provides a three-dimensional image by performing optical measurements, and it can be used in intra-vascular imaging. Related patents are U.S. Pat. No. 6,134,003, U.S. Pat. No. 6,010,449, and U.S. Pat. No. 5,459,570.

The opaqueness of blood at visible light wavelengths poses a specific problem when attempting to acquire an image of an intra-vascular space. One solution to the problem noted above is to utilize infrared (IR) light to enable visibility through the suspended particles and cells in the blood. A patent that discloses a method for using deep-IR light for imaging through blood is U.S. Pat. No. 6,178,346. The use of deep-IR wavelengths to achieve visibility in a blood medium as described in the referred patent requires very high-energy illumination, which has risks and disadvantages when used inside the body. The use of near-IR radiation substantially diminishes risks. U.S. Pat. No. 4,953,539 discusses the use of an endoscopic imaging device, which is illuminated from outside the body with infrared light. The referred patent serves as an example of the use of infrared light in imaging body organs. External illumination has not been used to date for intra-vascular imaging.

A well-known property of human tissue is that it has different absorption, scattering, and attenuation coefficients of IR radiation. This fact allows different types of tissues to be distinguished in general, and allows different types of plaque to be to be distinguished in particular. Reference is made to "A Review of the Optical Properties of Biological Tissues" Cheong, Prahl and Welch, IEEE J. of Quantum Electronics, Vol 26 No 12 December 1990.

SUMMARY

According to a first aspect of the present invention there is thus provided an invasive imaging apparatus comprising;
  i. A flexible catheter with a proximal end and a distal end, said distal end being shaped for insertion into a blood vessel along a guide wire thereby to reach remote places in the vasculature or other organs.
  ii. An optical assembly positioned at the distal end of said catheter comprising an image sensor positioned non-perpendicularly to the longitudinal axis of said catheter.
  iii. At least one illumination source for illuminating an immediate region beyond the distal end of said catheter.
  iv. At least one working channel running from the proximal to the distal end of said catheter.

Preferably said illumination source utilizes at least one wavelength taken from within a range comprising visible light, near infra-red, and infra-red light.

A preferred embodiment comprises a plurality of illumination sources and said illumination sources are controlled together.

A preferred embodiment comprises a plurality of illumination sources and said illumination sources are controlled separately.

Preferably said illumination source uses at least one wavelength preselected to improve visibility through blood.

Preferably said illumination source is comprised of an infra-red illumination source positionable outside of said patient's body.

Preferably said illumination source is controllable to be aimed directly at an imaged object from the direction of said imaging assembly.

Preferably said illumination source is controllable to be directed in a general viewing direction.

Preferably said optical assembly comprises optical components and an imaging assembly.

Preferably said imaging assembly comprises said image sensor and an illumination sensor.

Preferably said optical components comprise a lens with two optical planes, a shutter, and a light deflector.

Preferably said light deflector is one of a prism and a mirror with a reflecting surface.

Preferably said image sensor and said illumination sensor are operable to sense at least one wavelength taken from within a range from visible light to infra-red light to correspond to said illumination source.

Preferably a polarized filter is positionable before at least one of a member of a group comprising said illumination sensor, said image sensor, said illumination sources, and said lens, and said polarized filter polarization direction is controllable to enhance image quality.

A preferred embodiment comprises a central control and display unit connectable to the proximal end of said catheter from outside of the patient's body.

Preferably said working channel comprises a guide wire.

Preferably said working channel is usable for controllably passing through fluid to said distal end of catheter.

Preferably said image sensor is positioned substantially parallel to the longitudinal axis of said catheter.

Preferably said image sensor is shaped to fit within restricted dimensions of said catheter.

Preferably said image sensor is a CMOS or CCD-based pixel sensor.

Preferably said image sensor comprises an imaging area shaped in a rectangular pixel array.

Preferably said rectangular pixel array measures 128×256 pixels.

Preferably said sensor comprises sensor control electronic circuitry located beneath a shorter side of said imaging area, said imaging area being arranged as a rectangular pixel array.

Preferably I/O and supply pads for said electronic circuitry are placed along at least one of the shorter sides of said image sensor.

A preferred embodiment with a local controller located at the distal end of said catheter to coordinate data flow to and from said optical assembly and to perform commands received from said central control and display unit.

Preferably said display and control unit is operable to control the timing and amount of injection of said fluid.

Preferably a transparent balloon-like structure is positioned at said distal end of said catheter to displace blood from around the optical sensor-head, allowing clear visibility.

Preferably said balloon-like structure is rigid.

Preferably said balloon-like structure is flexible.

Preferably said balloon-like structure is inflated and deflated by means of using a liquid or a gas passed through said working channel.

Preferably said optical assembly comprises two image sensors for obtaining a stereoscopic image.

Preferably the injection of said fluid is synchronized with the operation of said optical assembly, synchronizing said operation and said injection with the cycle of patient physiological conditions.

Preferably one of said physiological conditions is heart beat sensible using a heart rate sensor (such as a plethysmograph, or other device) connectable to a patient's body from outside of said patient's body or insertable into said blood vessel through said catheter.

Preferably information from said heart rate sensor is transferred to said central control unit enabling synchronization with said physiological conditions.

Preferably said balloon-like structure is pressure-sensed to provide real-time feedback when said balloon-like structure impinges upon an obstacle, such as a blood vessel wall.

Preferably said working channel is usable for passage of therapeutic instruments to a site of operation.

Preferably said optical assembly is used in conjunction with a laser cutting device to enable laser operated surgery.

Preferably said laser cutting device is used to obtain biopsy biological samples by cutting and transferring through said working channel to the proximal end of said catheter.

Preferably said optical assembly and said laser cutting device are used in conjunction with one of a suction and nano-gripper mechanisms to enable visual inspection of a desired location for biological sample retrieval.

According to a second aspect of the present invention there is provided an invasive imaging control apparatus comprising:
 i. A flexible catheter with a proximal end and a distal end, said distal end being shaped for insertion into a blood vessel along a guide wire thereby to reach remote places in the vasculature or other organs.
 ii. An optical assembly positioned at the distal end of said catheter.
 iii. At least one working channel running from the proximal to the distal end of said catheter.
 iv. A control unit for regulating the opacity level of blood in said blood vessel around said distal end of said catheter, controllably injecting quantities of fluid into said blood vessel in the vicinity of said optical assembly, thereby enhancing visibility.

Preferably said optical assembly comprises an illumination sensor operable to sense at least one wavelength taken from within a range from visible light to infra-red light.

Preferably said working channel is usable for controllably passing through fluid to said distal end of catheter.

Preferably said control unit is connectable to the proximal end of said catheter from outside of the patient's body.

Preferably said control unit is operable to control the timing and amount of injection of said fluid.

Preferably the injection of said fluid is synchronized with the operation of said optical assembly, synchronizing said operation and said injection with the cycle of patient physiological conditions.

Preferably said fluid is insertable into the immediate region of said distal end of said catheter to change the optical characteristics of blood in said immediate region.

Preferably said fluid comprises one or more fluids selected to modify the optical characteristics of blood plasma to render said optical characteristics to be as close as possible to those of red blood cells.

Preferably said physiological condition is heart beat sensible using a heart rate sensor (such as a plethysmograph, or other device) connectable to a patient's body from outside of said patient's body or insertable into said blood vessel through said catheter.

Preferably information from said heart rate sensor is transferred to said central control unit enabling synchronization with said physiological conditions.

According to a third aspect of the present invention there is provided an invasive imaging control apparatus comprising:
 i. A flexible catheter with a proximal end and a distal end, said distal end being shaped for insertion into a blood vessel along a guide wire thereby to reach remote places in the vasculature or other organs.
 ii. An optical assembly positioned at the distal end of said catheter.
 iii. At least one working channel running from the proximal to the distal end of said catheter
 iv. A semi-permeable membrane positioned at said distal end of said catheter, surrounding said optical assembly extendable to displace blood from around the optical assembly allowing clear visibility.

Preferably said membrane is rigid.

Alternatively, said membrane is flexible.

Preferably said membrane is inflated and deflated by means of controllably passing a fluid through said working channel to said distal end of catheter.

A preferred embodiment has a control unit connectable to the proximal end of said catheter from outside of the patient's body.

Preferably the injection of said fluid is synchronized with the operation of said optical assembly, synchronizing said operation and said injection with the cycle of patient physiological conditions.

Preferably one of said physiological conditions is heart beat sensible using a heart rate sensor (such as a plethysmograph, or other device) connectable to a patient's body from outside of said patient's body or insertable into said blood vessel through said catheter.

Preferably information from said heart rate sensor is transferred to said central control unit enabling synchronization with said physiological conditions.

According to a fourth aspect of the present invention there is provided a method for performing biopsies and other diagnostic or therapeutic procedures comprising placing an invasive optical assembly apparatus on the distal end of a needle, inserting said optical assembly and needle into vasculature or other organs, and using said optical assembly to provide visual feedback of said biopsies and diagnostic or therapeutic procedures.

According to a fifth aspect of the present invention there is provided a method for viewing through blood in Situ comprising injecting a controlled amount of fluid into blood in the immediate region in front of an invasive optical assembly, temporarily changing the optical characteristics of the blood in said immediate region, and thereby improving visibility through said blood.

According to a sixth aspect of the present invention there is provided a method for viewing through blood in situ comprising injecting a controlled amount of fluid into blood in the immediate region in front of an invasive optical assembly, temporarily changing the reflectance of the liquid portion of said blood, and improving visibility through said blood.

Preferably said fluid is used to change the optical characteristics of blood in situ to facilitate imaging through said blood, said fluid being a physiological fluid, such as saline, or a hypoosmolar fluid, such as 0.45% saline or ⅙ saline.

Preferably said fluid for use in changing the optical properties of blood in situ to facilitate imaging through said blood, said fluid being a blood substitute which does not contain red blood cells and has homogenous optical characteristics.

Preferably said fluid is chosen to enable illumination to facilitate imaging through said blood and the environment in situ with an IR illumination source, enabling a frequency shift so that a visible light sensor can be effectively used.

Preferably said fluid is chosen to be oxygen carrying, such as a blood substitute, to reduce the risk of hypoxia to the heart muscle.

According to a seventh aspect of the present invention there is provided a method for reconstructing images by interpolating image data along at least one of the longitudinal and axial axes of a flexible catheter with a distal end inserted into a blood vessel and thereby reaching remote places in the vasculature or other organs, based on image data from both said longitudinal and axial axes, comprising:
 i. off-line image training initialization, and;
 ii. real-time image data interpolation.

Preferably said off-line image training initialization comprises:
  i. training image construction;
  ii. reconstruction of a lower resolution new image from said training image;
  iii. finding edge directions of said lower resolution image, and;
  iv. training a neural network to obtain a set of filters.

Preferably said training image is clipped and rotated to obtain robust edges in each one of a plurality of directions.

A preferred embodiment executing local contrast enhancement following said image data interpolation.

Preferably said local contrast enhancement comprises:
  i. calculating the average intensity of said real time image, yielding an intensity image;
  ii. generating a first image by correcting the intensity of said intensity image;
  iii. calculating a local contrast image;
  iv. generating a second image by enhancing said local contrast image, and;
  v. summing said first image and said local contrast image to generate an output image.

Preferably said first image is produced by modifying the intensity of said real time image using a lookup table.

A preferred embodiment comprises generating said second image by modifying the local contrast of said real time image using a lookup table. Preferably said real-time data interpolation comprises:
  i. finding edge directions of each pixel, and;
  ii. interpolating data using an appropriate direction filter from a set of direction filters.

A preferred embodiment comprises generating said set of direction filters in said off-line image training.

BRIEF DESCRIPTION OF THE DRAWINGS

For a better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Figure 1:
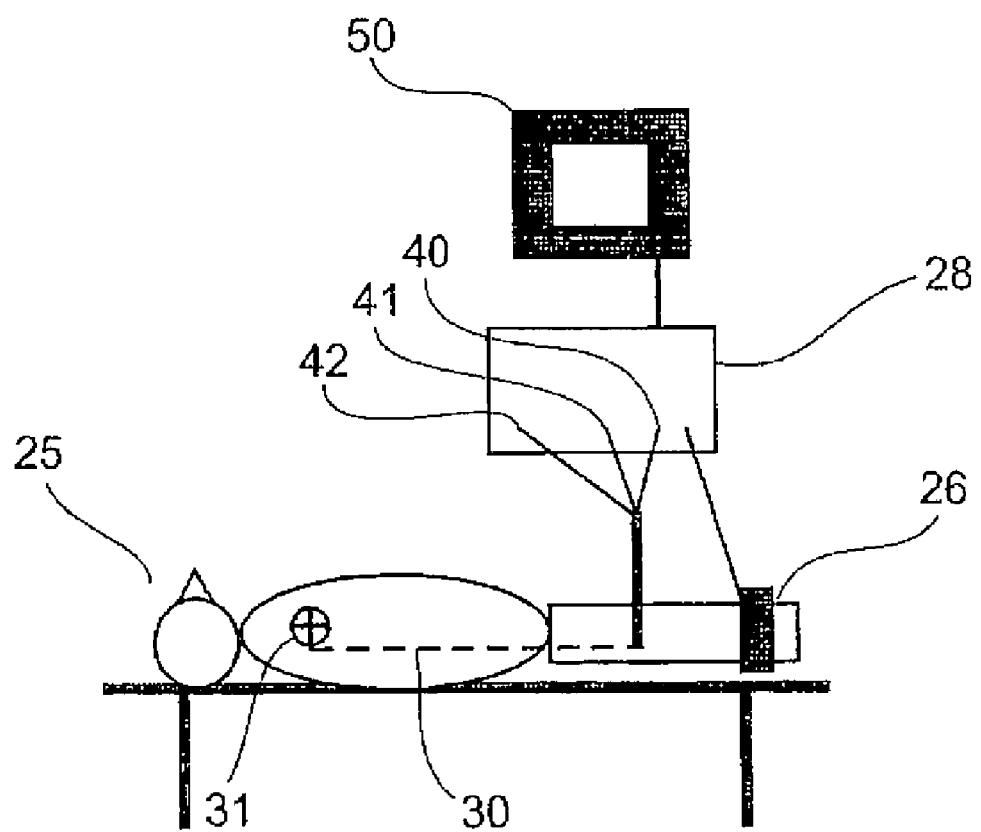
FIG. 1 is a simplified schematic of the overall patient system.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The present embodiments preferably provide a diagnostic and operative system for use in intra-vascular procedures. They consist of the following:

1. A small-diameter flexible catheter, with a distal end that can be inserted into the blood vessel or any other internal cavity along a guide wire and reach remote places in the vasculature or other organs; and
2. A viewing apparatus, which is positioned at the distal end of the catheter, and consists of a specifically designed image sensor, a distorting optical assembly and an illumination source.
   (a) The image sensor is shaped to fit within the restricted dimensions of the catheter. The image sensor is positioned non-perpendicularly to the longitudinal axis of the catheter; in a preferred embodiment parallel to the longitudinal axis of the catheter. The small width of the imaging area makes it possible to reduce the diameter of the catheter. The design of the sensor allows the catheter to contain both the viewing apparatus and a working channel without a prohibitive increase in catheter diameter.
   (b) An optical assembly. One preferred embodiment consists of a lens with two optical planes, a shutter and a prism or mirror with a reflecting surface. The optical assembly is designed to distort and deflect the light received from the viewed object to fit the sensor.
   (c) The light source or sources may be visible light sources, IR sources or any combination of the light sources in one embodiment, according to the embodiment's uses. The lighting is either aimed directly at the imaged object from the direction of the optical sensor head or directed generally at the scene, i.e. without directing the light sources straight ahead at the object.
3. One or more working channels, which run along the length of the catheter, from the proximal end to the distal end, through which therapeutic instruments can be inserted to the site of their operation. The working channel is also used for the injection of liquids or gas, as is described in some of the embodiments. A channel for a guide wire is necessary, and may be provided as a dedicated channel for the guide wire only or combined with a an injection channel.

4. A local controller situated at the distal head of the catheter for coordinating data flow to and from the optical image sensor head and carrying out commands coming from a central processing and control unit outside the body regarding, for example, shutter speed and changing the intensity of the light sources. The communication between the local controller and the central unit is conducted through a wire connection or a wireless connection. The local controller may be an entirely separate element situated at the distal head of the catheter as described above, but it also may be a part of the image sensor. Another option is that some or all of the local controller's functions are carried out by the central control and display unit described hereafter.

5. A central control and display unit is typically located on a rack in the operating/catheterization room. This unit executes, among other tasks, basic reconstruction of the image including color reconstruction, interface to the user, display of the video and additional data, manual/automatic control over image acquisition parameters, and a specific image reconstructing algorithm for improving resolution and local contrasts based on the specific design of the sensor.

The embodiments described are designed for use in both diagnostic and therapeutic procedures. Therefore, they can be used on catheters as a viewing device only or as part of a PTCA, scenting, laser, or any other operative device. Another option for combining intra-vascular imaging with the diagnostic and operative devices is by mounting the viewing apparatus at the distal end of a guide wire. The guide wire is inserted into the artery at the beginning of a catheterization procedure, and the guide wire guides the catheters used during the procedure to their proper location. The positioning of the imaging apparatus on a guide wire makes it possible to use it in very restricted spaces. Positioning of the imaging apparatus on the guide wire also allows better navigation inside the vessel and the replacement of the diagnostic and operating tools while keeping an insertion path open by means of the wire.

Reference is now made to FIG. 1, which is a simplified schematic of the overall patient-system configuration according to a first preferred embodiment of the present invention. The configuration has a processing and control unit 28 comprising, among others, three functional units: digital video unit 40; balloon inflation unit 41; and fluid injection unit 42. The proximal end of the catheter 30 is connected to the processing and control unit 28. The display unit 50 (typically a monitor) is also connected to the processing and control unit 28. The catheter 30 is inserted into the patient 25 with the inflatable balloon 31 located at the catheter distal end, inside the patient. A heart rate sensor 26 is connected to the patient.

The heart rate of the patient 25 is monitored either by a heart rate sensor 26 attached to the patient or by a method described below to determine the transparency level of the blood. (Such a measurement can indicate blood pressure changes, and is correlated to heart activity.) Information about the heart rate is sent to the processing and control unit 28. The processing and control unit receives the information, processes it and synchronizes the system's operation with the heart rate. The catheter 30 is connected to the processing and control unit through three channels: digital video 40, balloon inflation 41 (for inflating and deflating the inflatable balloon 31 located at the distal end of the catheter 30, located inside the patient) and fluid injection 42 (used to inject fluids to alter the optical quality of the blood in the immediate vicinity of the inflatable balloon 31).

Figure 2A:
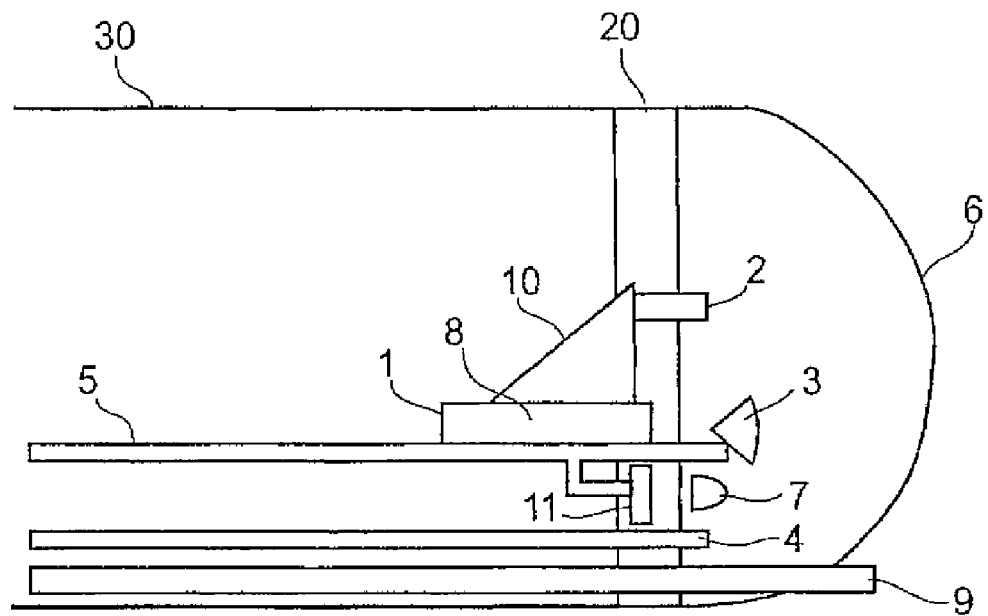
FIG. 2A is a simplified schematic of the optical head—side view.
Figure 2B:
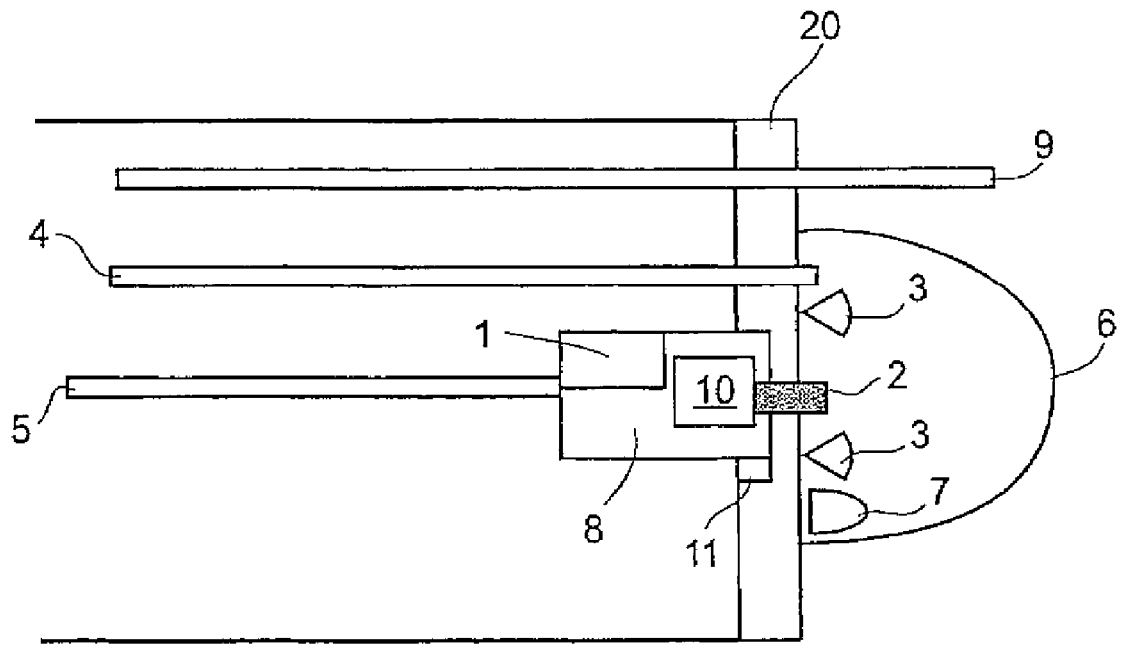
FIG. 2B is a simplified schematic of the optical head—top view.

Reference is now made to FIGS. 2A and 2B which are schematic details of a side view and a top view, respectively, of the optical head, located on the distal end of the catheter 30. The optical head comprises a lens 2 and an optical array, comprising a prism 10, and a sensor array, comprising a light sensor 8 and an image sensor 1 (for acquiring images). The light sensor 8 and image sensor 1 may be separate elements or they may be combined together. One or more illumination sources 3, which may use visible or infrared or both types of light, are positioned at the distal end of the optical head. A pressure sensor 7 is also positioned at the distal end of the optical head. A variable volume transparent balloon 6 encloses all components on the distal end. A mechanical enclosure houses the previously mentioned components and serves as the proximal surface of the variable volume transparent balloon 6. Working channel A 4, representing one or more such channels, runs along the catheter 30 and terminates at the distal end inside of the variable volume transparent balloon 6. Working channel B 9, representing one or more such channels, runs along the catheter 30 and terminates distally outside of the variable volume transparent balloon. A cable 5 runs along the catheter 30 and connects with the local controller 11 and provides power and communications for the optical head.

The illumination sources 3 in the present embodiment illuminate the region immediately in front of the optical head. DC power and electrical signals are fed to and from the optical head via the cable 5 which is connected at the distal end to the local controller 11. Working channels (in this example, two) provide fluid feed and removal and/or other functions inside and outside of the variable volume transparent balloon 6.

The variable volume transparent balloon 6 enables short period imaging of a blood vessel (for example) using the visible and/or infrared illumination sources 3. The variable volume transparent balloon pressure is sensed and controlled by the pressure sensor 7 to inflate/deflate the balloon via air or liquid provided through working channel A 4. The system has a fixed optical mechanism comprised of a lens 2 and a prism 10. The variable volume transparent balloon 6 has known optical attributes and it enables close contact with the blood vessel wall. Inflation of the variable volume transparent balloon 6 enables a clear path for the visible or infrared light directly onto the lens 2. When deflated, the variable volume transparent balloon 6 allows an undisturbed flow of blood until the moment before an image is acquired, whereupon the variable volume transparent balloon 6 is inflated again. At the time of variable volume transparent balloon 6 inflation, blood flow is momentarily disturbed to enable a clear view. A safety mechanism, comprising a pressure sensor 7 ensures that pressure within the balloon is maintained at acceptable limits. The combination of the pressure sensor 7 and the momentary pressure supply provide an indication of a possible obstacle in the path of the catheter. A local controller 11 coordinates data flow to and from the optical head, as is described in more detail below.

Figure 3:
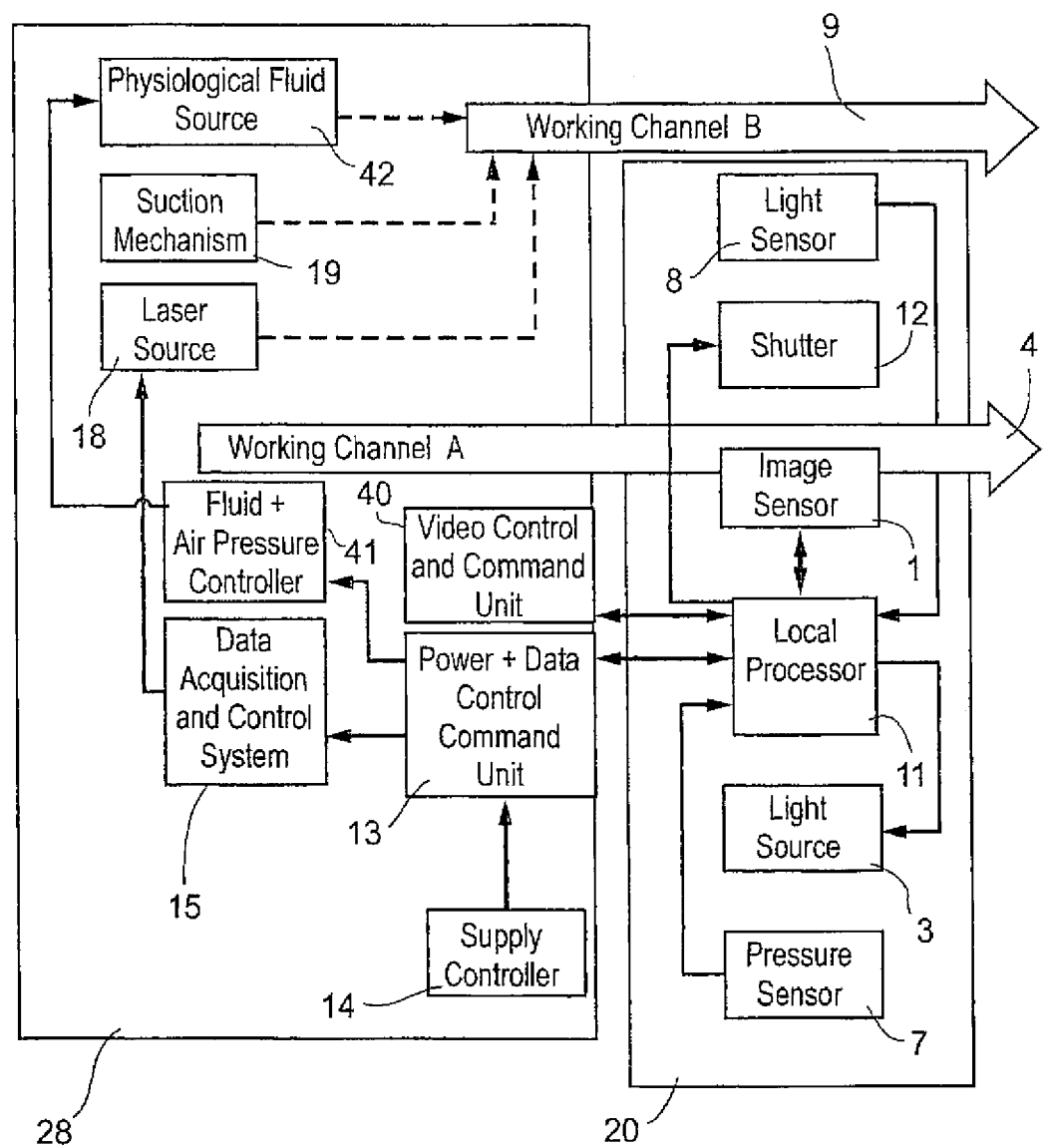
FIG. 3 is a system block diagram.

Reference is now made to FIG. 3, which is a system block diagram. FIG. 3 highlights the logic in and between the optical head 20, as detailed in FIGS. 2A and 2B, with the processing and control unit 28, as described in FIG. 1. The functions of the optical head 20 are grouped logically in FIG. 3. The local processor 11 serves to control the functions of the optical head 20 while coordinating signals and power with the processing and control unit 28 located in the operating room. Functions of the optical head 20 are the illumination source 3 (commanded by the local processor 11), light sensor 8 (which feeds back to the local processor 11), image sensor 1 (which feeds back to the local processor 11), and shutter 12 (commanded by the local processor 11). The local processor 11 receives and sends commands and receives power from the video control and command unit 40 and power and data control command unit 13, both of which are located in the processing and control unit 28. The video control and command unit 40 and power and data control command unit 13 together form the core of command and control of the entire system. Additional functions are: supply controller 14 (power supply to power and data control 13), data acquisition and control system 15 (commanded by power and data control unit 13), and the fluid and air pressure controller 41 (commanded by power and data control unit 13). The fluid and air pressure controller 41 operates through working channel A 4, which physically passes through the optical head to enable balloon inflation. In addition, the fluid and air pressure control 41 commands the physiological fluid control source 42. The suction mechanism 19 and laser source 18 all function through working channel B 9, which runs along the catheter but parallel and external to the optical head. The suction mechanism 19 and laser source 18 are devices that may be employed in an embodiment described below.

The local processor 11 controls and coordinates functioning of components previously described on the optical head with the system control and supply functions located in the operating room. Specific functions of the power and data control unit 13 include, timing control of the system functions such as timing of balloon inflation, fluid infusion/injection, activation of light sources 3, and image sensor 1 activation. The video control and command unit 40 receives digital image information from the image sensor 1. Corrections of optical distortion created by the image sensor 1 taking into account the system overall design, are controlled by the video control and command unit 40. Other functions controlled by the video control and command unit 40 are:

1. Improvement of image resolution based on redundant information residing in the system, intended specifically for improving image resolution.
2. Improvement of image quality and image adjustment for the specific medical application, for example: color, local contrasts, and emphasis on pathologies.
3. Evaluation of relative temperature based on video information for spotting pathologic areas suspected as inflamed.
4. Evaluation of the blurring parameters of the image based on the blurring model of the blood and the acquired image.
5. Reconstruction of the original image according to the blurring model and evaluated parameters.

Images processed by the video control and command unit 40 may be displayed, typically on the previously mentioned monitor, as video images in one of two display modalities. The first modality is a succession of separate images as received by the image sensor 1. This modality requires a minimal delay. The second modality is a stream of video images. In order to enable a stream of video images the processing and control unit 28 performs a time interpolation of missing images to provide a continuous image. As a result, a delay of up to a second between image acquisition and display is typical.

Figure 4A:
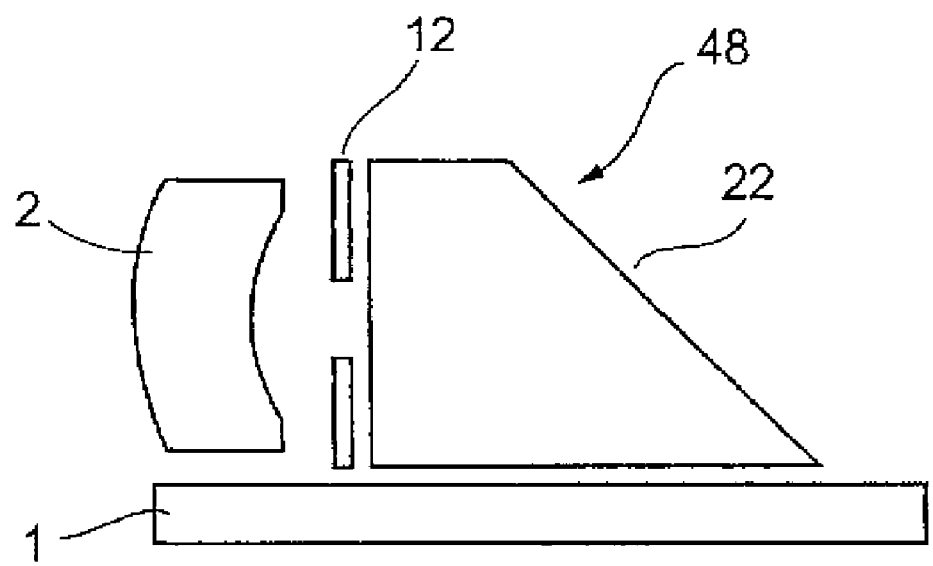
FIG. 4A is a simplified schematic of the optical array assembly.
Figure 4B:
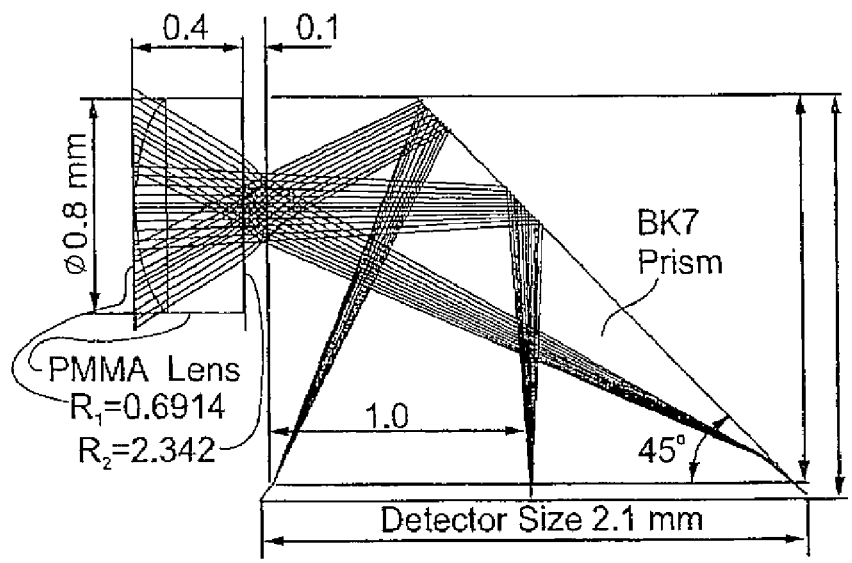
FIG. 4B is a schematic example configuration of optical design A.
Figure 4C:
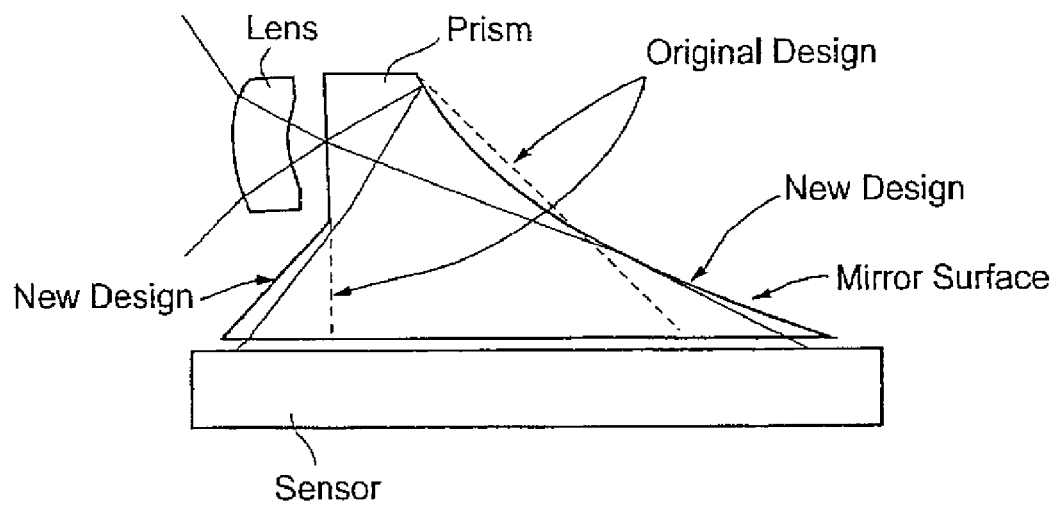
FIG. 4C is a schematic example configuration of optical design B.

Reference is now made to FIG. 4A, which shows a schematic of the optical array assembly. The optical array assembly 48 is comprised of a lens 2 which is located in front of the shutter 12, which is in turn mounted before the prism 22. The prism is positioned above the image sensor 1. One preferred embodiment consists of a lens 2 with two optical planes, a shutter 12 and a prism 22 or mirror with a reflecting surface. The optical array assembly 48 is designed to distort and deflect light received from the viewed object to fit the image sensor 1. The lens 2 and prism 22 are two fixed optical components whereas the shutter 12 offers flexibility. The shutter 12, as previously mentioned, is commanded by the processing and control unit, located outside of the patient at the proximal end of the catheter in the operating room. Schematic descriptions of two optical design alternatives are depicted on FIGS. 4B and 4C. In FIG. 4B PMMA refers to a specific plastic lens material called polymethyl methacrylate.

Figure 5A:
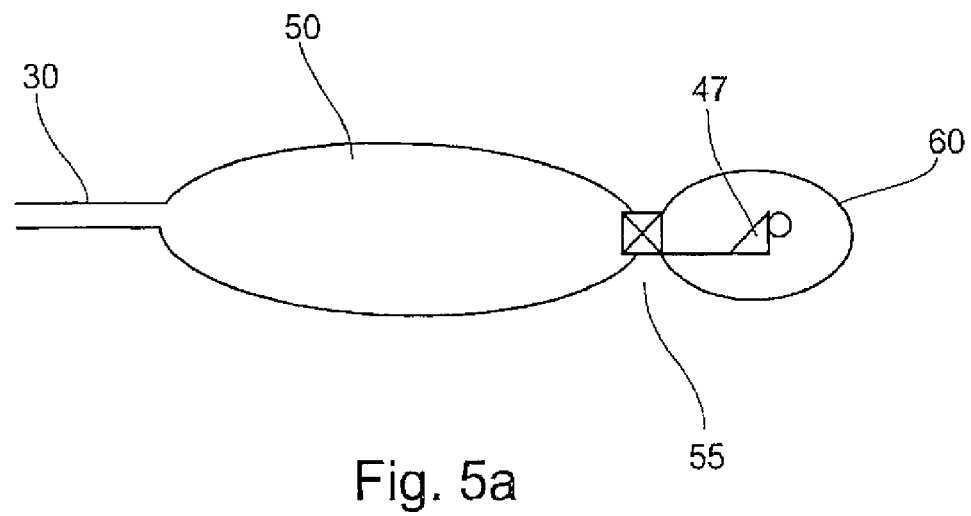
FIG. 5A is a simplified diagram of a configuration with the optical head inside of a transparent balloon distal to a PTCA/stent balloon.
Figure 5B:
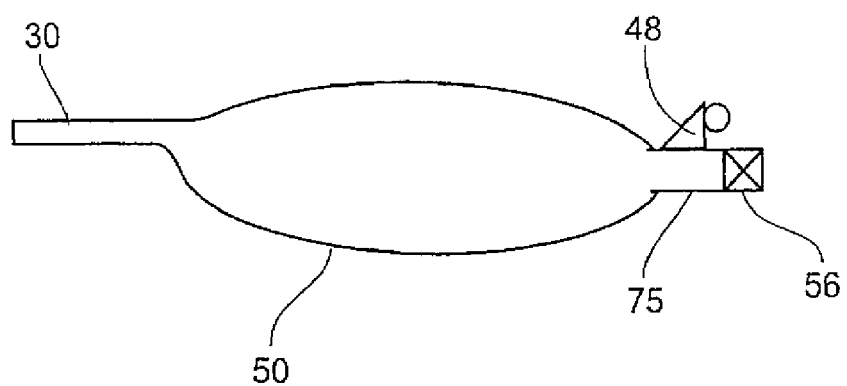
FIG. 5B is a simplified diagram of a configuration with the optical head adjoining the PTCA/stent balloon.

Reference is now made to FIGS. 5A and 5B, which show related embodiments where a fluid is used to inflate the flexible PTCA or stenting catheter balloon at the distal end of the catheter. FIG. 5A shows an embodiment where an optical head 47 is located distally to the PTCA/stent balloon 50. The stent balloon 50 is located distally to the catheter 30. The optical head 47 is located within a second balloon 60. A regulating valve 55 is located between the PTCA/stent balloon 50 and the second balloon 60. Inflation of the second balloon 60 is enabled by the regulating valve 55, which allows the second balloon 60 to be initially inflated, followed by inflation of the stent balloon 50. Note that the optical head shown in FIG. 5A is similar to the optical head previously shown in FIG. 2, in that the functions of on-board multiple light sources, on-board light receivers, and on-board pressure sensor are preferably included. The regulating valve 55 is designed to close itself under high pressure and enables the inflation of the PTCA/stent balloon 50. Once the second balloon 60 is inflated and the pressure inside is high enough, the valve closes and the PTCA/stent balloon 50 inflates. The injected fluid inflates the second balloon 60, made of a transparent membrane which is non-permeable to red blood cells, to remove the red blood cells from the field of view and reduce the scattering of light. The optical characteristics of the injection fluid are discussed hereafter. The regulating valve 55 also controls deflation of both the PTCA/stent balloon 50 and the second balloon 60, FIG. 5B shows an embodiment where the optical head 48 is installed distally and exterior to the PTCA/stent balloon 50. The optical head assembly 48 is mounted on the fluid injection channel 75, which terminates in a regulating valve 56, located at the distal end of the fluid injection channel 75. The PTCA/stent balloon 50 is located at the distal end of the catheter. Note that the optical head assembly 48 shown in FIG. 5B is similar to the optical head previously shown in FIG. 2 in that the functions of on-board multiple light sources and on board light receiver are preferably included. In the present embodiment, a regulating valve 56 located distally to the PTCA/stent balloon 50 controls the flow of injected fluid distally outside of the PTCA/stent balloon 50 to momentarily clear the field of view in front of the optical assembly and allow images to be acquired.

The embodiments shown in FIGS. 5A and 5B operate in a cyclical manner. Every heartbeat sensed by the previously mentioned heart rate sensor, initiates a new device cycle. Each cycle comprises a delay after which fluid is injected in order to inflate the second balloon 60 as in FIG. 5A or clear the field of view as in FIG. 5B. Inflation of the second balloon 60 and fluid injection are synchronized and timed so that they occur after a pulse of blood which is pushed from the heart. The regulating valve 56 is opened and fluid is infused into the artery to improve the visibility at the distal end of the catheter. A short period after the start of fluid infusion, the optical head assembly 48 starts acquiring images of the scene. The previously-mentioned light sources are powered in synchronized pulses with the frame rate of the optical head assembly 48 to increase the ratio between the effective light absorbed by the optical head assembly 48 and power dissipation of the light source. After obtaining several images and in synchronization with the beginning of the next heart beat, the system stops both image acquisition and infusion of fluid and reduces the pressure inside the second balloon 60.

The embodiments shown in FIGS. 5A and 5B are not space-consuming because one channel is used for inflating both balloons (FIG. 5A) or for inflating and injecting fluid into the blood vessel (FIG. 5B), thus allowing a smaller width catheter.

Figure 6:
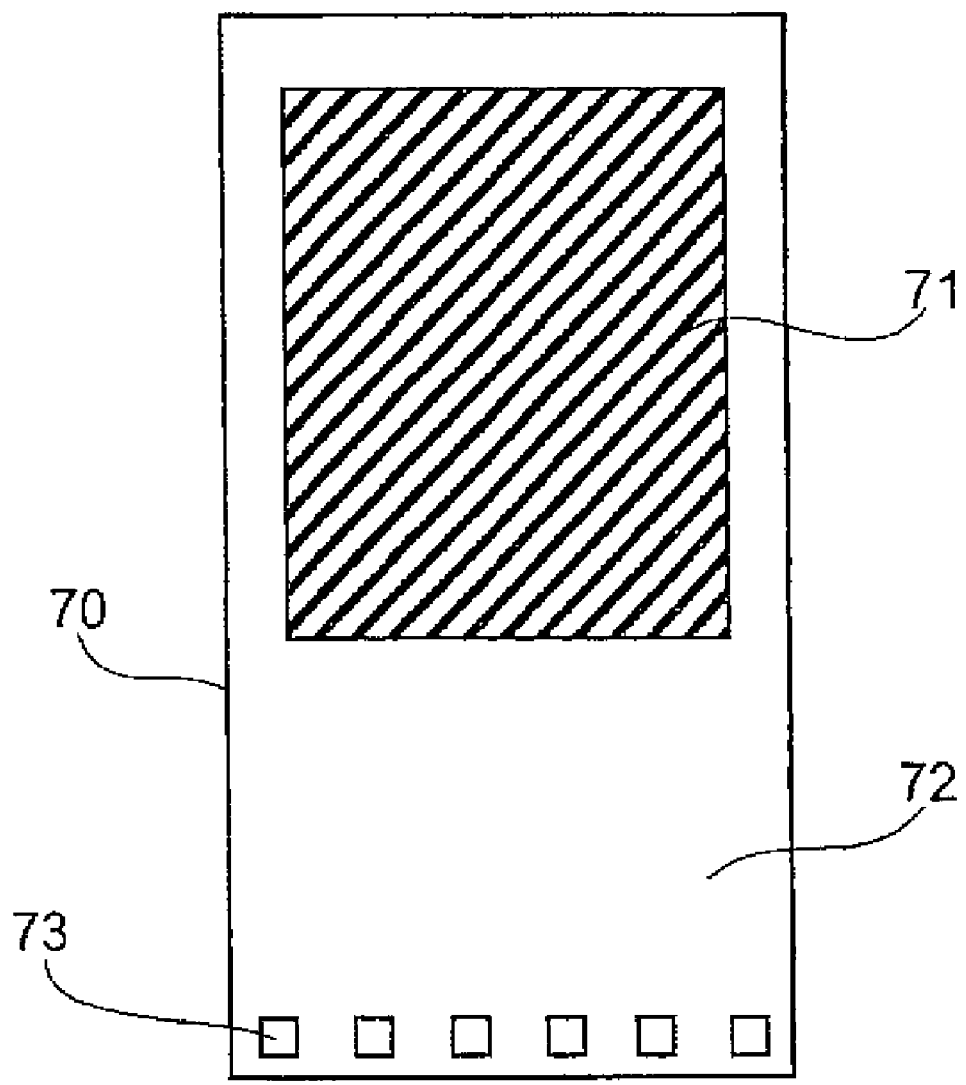
FIG. 6 is a schematic representation of the image sensor.

Reference is now made to FIG. 6, which is a simplified diagram showing an image sensor 70. The sensor comprises an imaging area 71 which is shaped as a rectangle pixel area, such as a 128×256 pixel array. The sensor may also contain additional circuitry 72 that performs functions such as analog to digital conversion, timing control, and local control. I/O supply pads 73 are shown in this example below circuitry 72 along the short side of the rectangular sensor. The sensor 70 is located in the optical head assembly previously noted in FIGS. 2, 3, and 4A, 4B, and 4C. The sensor 70 serves to capture the visible or IR light from the scene as shaped by the lenses and shutters located in front of it. As previously noted, the sensor is positioned non-perpendicularly to the longitudinal axis of the catheter. In a preferred embodiment it is placed parallel to that axis. The small width of the imaging area makes it possible to reduce the diameter of the catheter.

Figure 7:
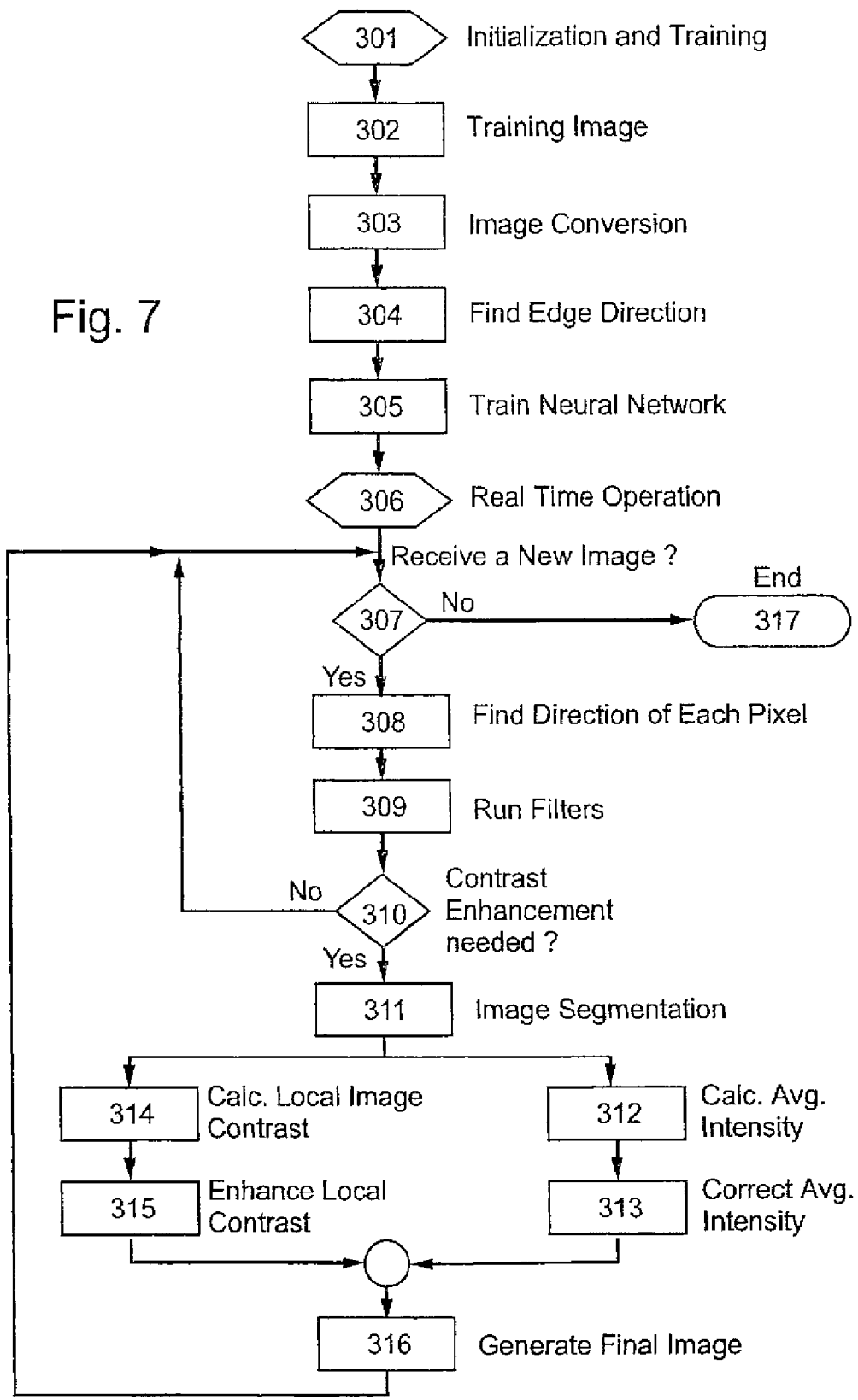
FIG. 7 is a block diagram of the post processing algorithm.

Reference is now made to FIG. 7. FIG. 7 is a simplified block diagram describing a post-processing algorithm, which reconstructs the displayed image based on a training sequence and a real time image, once an image has been received by the central control and display unit. The central control and display unit is preferably located in the operating room, and it receives images from the image sensor, preferably located at the distal end of the catheter, preferably located in a blood vessel.

The initialization and training sequence 301 takes place as a one-time off-line process. The aim of this sequence is to determine the optimal set of filters for reconstructing the real-time image. The sequence begins by construction of a training image, followed by clipping and rotating the image to obtain robust edges in all directions 302. For illustration purposes the training image size may be N by N pixels. Then, pre input image conversion 303 takes place involving construction of a new image from the training frame in order to obtain an input to a neural network. The input image size selected for this case is N/2 by N pixels, but the algorithm works with other image sizes. Input image conversion 303 is then performed by finding the edge direction 304 at each pixel of the input according to neighborhood decision vote, followed by training the neural network 305 to obtain a set of filters. The training process is performed on the intensity image (a black and white gray level image). The result at this point is a set of filters (weights) to be used on the real-time sequence.

Real-time execution begins with step 306, when a new image is received 307. If there are no more images, execution is completed 317. If a new image is received, the next step is to find the direction for each pixel 308 in the intensity input image according to the neighborhood decision vote. The neural networks' filters are then run 309, in accordance with the directions for each color plane, which is performed separately. If contrast enhancement is necessary 310, a series of steps are performed, as noted below. If contrast enhancement is not necessary, a new image is received 307.

The first step of contrast enhancement is to perform image segmentation 311 based on local average intensity. The following steps are performed: calculate average intensity 312, taking into account only neighbors with relatively close values, and; correct average intensity 313 using look up tables (LUT) which optimizes the dynamic range of the system (camera and display device). In parallel to the two previous steps, the following are performed: calculate local image contrast 314 and; enhance local contrast 315. The enhancement function is a function of the average intensity and the local contrast and it is done by means of LUT. Generation of the final image 316 utilizes the previous steps of contrast and intensity enhancement, summing the local contrast and the average intensity. At this point, a new image is received 307. This logic continues until there are no new images and the algorithm ends 317.

Methods for Imaging in the Presence of Opaque Liquids

The following are various preferred embodiments for different methods and applications designed to achieve visibility through a medium of an opaque liquid, preferably, in blood. It is important to emphasize that the various embodiments described below can be used either separately as stand-alone systems or in any combination with each other.

1. Lighting with Near-IR Wavelengths:

There are three properties of light that effect the visibility of light with a specific wavelength passing through a medium: scattering, absorption, and attenuation. Scattering is significant in both near-IR and visible light when passing through blood. Absorption and attenuation, on the other hand, are minimal in near-IR radiation. Therefore, near-IR light may be advantageous when compared to visible light for effective illumination through such a medium as blood. In the following text, it should be noted that wherever IR is mentioned, near-IR (radiation with wavelengths shorter than 1 μm) is preferably used, unless specified otherwise.

The fact that IR light absorption is minimal in a blood medium means that IR light may be used in a viewing apparatus designed for intra-vascular imaging in combination with other methods mentioned in the present disclosure. The apparatus and method in the present embodiment includes a flexible catheter with a viewing apparatus at its distal end, a working channel running from the proximal to the distal end, and a local controller at the distal end. The previously mentioned imaging sensing apparatus is applicable to the present embodiment. The apparatus consists of one or more light sources which emit IR light, an image sensor that is able to receive this light, and an optical assembly. The image sensor is preferably a CMOS or CCD pixilated sensor. In order to allow acquisition of IR images, the sensor may use filters that have band passes at IR wavelengths. Silicon-based devices (CMOS, CCD) exhibit a reasonably good response to IR wavelengths of up to 1 μm.

The light sources may also include a combination of wavelengths of visible and IR light, requiring appropriate sensors to receive multiple light wavelengths. Illuminating the scene with multiple wavelength light sources enables acquisition of several types of pictures for diagnostic purposes.

IR light can be used in another diagnostic embodiment, considering the fact that in general, different human tissues and different substances have different absorption, scattering, and attenuation coefficients in the IR region. The present embodiments can include an analyzing apparatus for the analysis of these coefficients. Evaluation of blood status (for example, sugar level in the blood may be analyzed by evaluating the IR light absorption) may be one of the applications of the present embodiment. Several pathologies in the vessel tissue may be analyzed in the same way.

Figure 8:
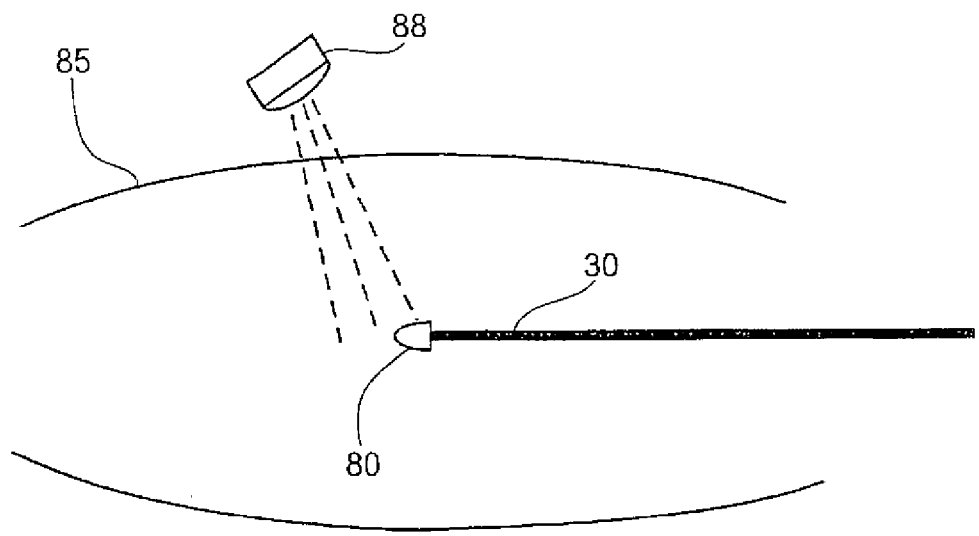
FIG. 8 is a simplified schematic of use of an external IR source.

Another embodiment uses external IR illumination. Reference is made to FIG. 8. The optical head assembly 80 is located at the distal end of the catheter 30 within the patient's body 85, preferably in a blood vessel. An exterior IR light source 88 exterior to the patient's body illuminates the field of view in front of the optical head assembly. Note that the optical head assembly 80 shown in FIG. 8 is similar to the optical head assembly 20 previously shown in FIG. 2 in that the function of on-light receiver is preferably included. However, in the present embodiment, the light source is not on-board the optical head assembly 80, rather it is exterior to the patient.

2. Changing the Optical Properties of Blood

Another method and embodiment makes use of light sources utilizing visible light or IR radiation. Blood is opaque in visible light illumination because blood contains suspended cells. This phenomenon is much like that encountered with water vapor drops in fog; even though the content of the red blood cells is transparent, when the content of red blood cells is arranged in "drops" surrounded by a membrane, the reflectance factor of the solution yields an opaque situation. Therefore, in order to obtain a clear vision of the field of view, blood may be temporarily diluted at the site of an object to be imaged.

The injection fluid is not necessarily a physiological fluid. One possible embodiment uses a fluid with a reflectance factor identical or similar to the reflectance factor of red blood cells, or a fluid that creates such a reflectance factor when mixed in a certain concentration with blood. This type of fluid solves the problem of light scattering in blood, leaving only a light absorption problem, which is much simpler to solve. The present embodiment includes a flexible catheter, a viewing apparatus and a local controller at the distal end and a working channel, through which the fluid may be injected from the proximal end into the blood vessel or injected directly into the vessel. Another option is to inject the fluid through the guide wire channel. The amount of injected fluid is controlled centrally by a processing device, and is determined according to the transparency level of the blood, measured by the reflection of illumination from the light source onto the light sensor as previously described, or according to a sensor connected to the patient outside of the patient's body. Such a light measurement may supply the timing to inject the physiological fluid into the vessel. In another application, the reflected light measurement may provide for analysis of blood pressure changes by measuring the amplitude of the light reflected into the sensor, according to the level of heart activity. There is a correlation between the amplitude of light received by the sensor and blood pressure.

Variations in the amount and timing of fluid injection may be determined by a quality control algorithm, which may be able to calculate necessary changes to lighting or fluid injection from the received image to improve image quality.

A further embodiment of the present invention uses either a fluid with a physiological concentration of particles or a fluid with less than a physiological concentration of particles, such as ⅙ saline. The latter type of fluid can cause hemolysis of some of the red blood cells, thus improving the reflectance factor of the liquid, and reducing the above-mentioned phenomenon of light scattering in blood. Another embodiment uses a fluid that is capable of carrying oxygen, such as a blood substitute, thus reducing the risk of hypoxia to the heart muscle; this compared to injecting a fluid not capable of carrying oxygen to body tissues into the artery.

Yet another embodiment uses a fluid that enables a frequency conversion of light, i.e. from IR wavelengths to the visible light spectrum, thus making it possible to use a visible light optical sensor and nevertheless retaining the advantages of illuminating with IR light.

3. Transparent Structure at the Distal End

The present embodiment also makes use of light sources in the visible light or IR wavelengths. There is a need to displace the blood in order to clear the field of view. This embodiment uses a transparent dome or balloon, either rigid or flexible. The structure is positioned at the distal end of the catheter, beyond the viewing apparatus. In one form of the embodiment previously described and referred to in FIGS. 5A and 5B, the structure at the distal end is a flexible balloon, which inflates by injecting a transparent fluid or gas into it. It is positioned at the distal end of the catheter at its deflated mode. The injection is preferably, centrally controlled and the fluid or gas may be injected to inflate the balloon whenever the viewing apparatus is activated. When inflated, the balloon displaces the blood from the field of view, as does the dome described above. In another form of the embodiment, the structure is a rigid dome, which is positioned around and at the edge of the distal end and extends distally to it. The rigid structure is situated so that it removes the blood from around the viewing apparatus, thus clearing the field of view between the dome and the apparatus without blocking the flow of blood in the artery. The rigid structure is either hollow (vacuum, gas) or filled with a transparent fluid.

4. Polarized Light Filter

Light that impinges on a surface has a component that returns polarized. Reflected light is more polarized when the incidence angle is closer to normal. In an intra-vascular surrounding, light hitting the wall and/or any structures connected to it returns mostly polarized, while the light hitting suspended cells in the fluid filling the vessel does not return polarized. Imaged objects are usually surfaces connected to the vessel's wall. As a result, by situating a polarized light filter before the optical assembly, light reaching the sensor may be only polarized light, i.e. the light reflected from the imaged structure. This method of using polarized light increases the image/noise ratio and improves the quality of the received image.

Other Possible System Embodiments

Figure 9:
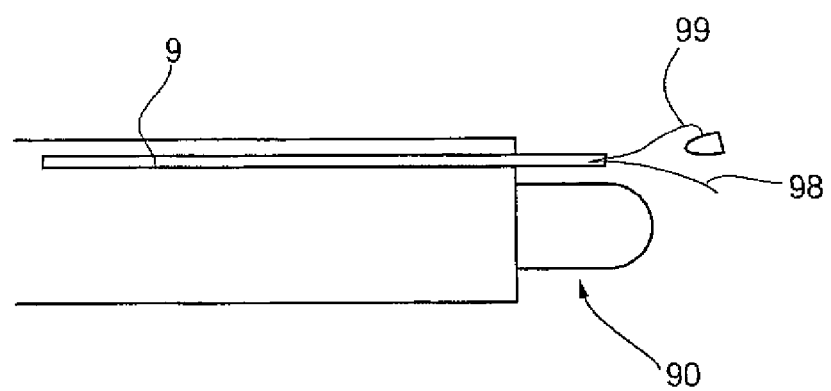
FIG. 9 is a simplified schematic of a biological sample collector.

In addition to the embodiments previously discussed, the following represent four other possible embodiments, related to previously described embodiments:

1. An optical sensor head with two sensors for obtaining a stereoscopic image.
2. A distal balloon made of a transparent membrane blocking the passage of red blood cells but allowing the passage of fluids. In the present embodiment, the injected fluid can also be used for the inflation of the distal balloon membrane.
3. Laser operated surgery mechanism using service channel and local imaging device(s). This embodiment enables an accurate operation procedure with continuous imaging of the operation area.
4. Mounting the viewing apparatus close to the front end of a needle for performing biopsies and other diagnostic or therapeutic procedures.
5. Another embodiment is that of biopsy and sample retrieval. Reference is made to FIG. 9. Working channel B 9 is used to pass either or both the suction and nano-gripper 98 and the laser device 98 distally, in front of the optical head 90. Biological sample collection, using a suction/nano-gripper 99 mechanism and the optical head 90 to enable visual inspection of the desired location. Samples may be transferred through the working channel B 9 outside the patient's body for analysis. The suction/nano-gripper 99 is used to hold a sample in position and the laser apparatus is used to cut the sample from surrounding tissue. The optical head 90 is similar to the previously mentioned optical head configuration. The suction/nano-gripper 99 and laser device 98 can alternately or together be positioned in front of the optical head 90 to provide visual feedback. This process enables biopsy of samples which can be removed from the patient's body through working channel B 9.

The application in the field of cardiovascular therapy is only one of the possible applications for the present invention. Minimally invasive surgery is applied in many fields of medical diagnosis and therapy, such as in other vascular, breast, urethral and renal, and abdominal procedures, for example, and the present invention may be applied in these fields.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub combination.

It will be appreciated by persons skilled in the art that the present invention is not limited to what has been particularly shown and described hereinabove. Rather the scope of the present invention is defined by the appended claims and includes both combinations and sub combinations of the various features described hereinabove as well as variations and modifications thereof which would occur to persons skilled in the art upon reading the foregoing description.

The invention claimed is:

1. An invasive imaging control apparatus comprising:
   i. a flexible catheter with a proximal end and a distal end, said distal end being shaped for insertion into a blood vessel along a guide wire thereby to reach remote places in the vasculature or other organs;
   ii. an optical assembly positioned at the distal end of said catheter;
   iii. at least one working channel running from the proximal to the distal end of said catheter;
   iv. a control unit, that is not inserted into the blood vessel with the catheter, for regulating the opacity level of blood in said blood vessel around said distal end of said catheter, controllably injecting quantities of fluid into said blood vessel in the vicinity of said optical assembly, thereby enhancing visibility;
   v. a local controller located at the distal end of the catheter for controlling data flow to and from an optical head at the distal end portion of the catheter, the optical head comprising an image sensor and at least one of an illumination source, a light sensor, or a shutter, and wherein the local controller is configured to control one or more functions of the optical head while coordinating signals and power with the control unit and the functions of the optical head being selected from the group consisting of (1) commanding the illumination source, (2) accepting signals from the light sensor, (3) accepting signals from the image sensor, and (4) commanding the shutter; and
   wherein said optical head comprises a light sensor operable to sense at least one wavelength taken from within a range from visible light to infra-red light.

2. A method for viewing through blood in situ comprising:
   placing at least a distal end portion of a medical instrument into a blood vessel;
   injecting a controlled amount of fluid into blood in the immediate region in front of an optical assembly included on the distal end portion of the medical instrument presented in the blood vessel;
   controlling data flow to and from an optical head at the distal end portion of the medical instrument, the optical head comprising a local controller which is included in the distal end portion of the medical instrument, the optical head comprising an image sensor and at least one of an illumination source, a light sensor, or a shutter, and wherein the local controller serves to control one or more functions of the optical head while coordinating signals and power with a central control unit that is not inserted into the blood vessel, and the controlled functions of the optical head being selected from the group consisting of (1) commanding the illumination source, (2) accepting signals from the light sensor, (3) accepting signals from the image sensor, and (4) commanding the shutter,
   temporarily changing the amount of fluid injected in front of the optical assembly based on the data flow received from the optical head; and
   wherein said fluid is used to change the optical characteristics of blood in situ to facilitate imaging through said blood, said fluid being a hypoosmolar fluid.

3. The method of claim 2 wherein the hypoosmolar fluid is 0.45% saline.

4. The method of claim 2 wherein the hypoosmolar fluid is ⅙ saline.

5. A method for viewing through blood in situ comprising:
   placing at least a distal end portion of a medical instrument into a blood vessel;
   injecting a controlled amount of fluid into blood in the immediate region in front of an optical assembly included on the distal end portion of the medical instrument presented in the blood vessel;
   controlling data flow to and from an optical head at the distal end portion of the medical instrument, the optical head comprising a local controller which is included in the distal end portion of the medical instrument, the optical head comprising an image sensor and at least one of an illumination source, a light sensor, or a shutter, and wherein the local controller serves to control one or more functions of the optical head while coordinating signals and power with a central control unit that is not inserted into the blood vessel, and the controlled functions of the optical head being selected from the group consisting of (1) commanding the illumination source, (2) accepting signals from the light sensor, (3) accepting signals from the image sensor, and (4) commanding the shutter;
   temporarily changing the amount of fluid injected in front of the optical assembly based on the data flow received from the optical head; and
   further comprising running a post processing algorithm that starts with formation of a training image and that allows generation of a final image based on communications of the local controller and the central control unit.

6. The method of claim 5 wherein the post processing algorithm reconstructs a displayed image based on a training sequence and a real time image.

7. The method of claim 5 wherein the post processing algorithm generates the final image utilizing the steps of contrast and intensity enhancement.

8. An invasive imaging control apparatus comprising:
   i. a flexible catheter with a proximal end and a distal end, said distal end being shaped for insertion into a blood vessel along a guide wire thereby to reach remote places in the vasculature or other organs;

ii. an optical assembly positioned at the distal end of said catheter;

iii. at least one working channel running from the proximal to the distal end of said catheter;

iv. a control unit, that is not inserted into the blood vessel with the catheter, for regulating the opacity level of blood in said blood vessel around said distal end of said catheter, controllably injecting quantities of fluid into said blood vessel in the vicinity of said optical assembly, thereby enhancing visibility;

v. a local controller located at the distal end of the catheter for controlling data flow to and from an optical head at the distal end portion of the catheter, the optical head comprising an image sensor and at least one of an illumination source, a light sensor, or a shutter, and wherein the local controller is configured to control one or more functions of the optical head while coordinating signals and power with the control unit and the functions of the optical head being selected from the group consisting of (1) commanding the illumination source, (2) accepting signals from the light sensor, (3) accepting signals from the image sensor, and (4) commanding the shutter; and wherein the optical head includes a light source and the local controller controls the light source.

9. An invasive imaging control apparatus comprising:

i. a flexible catheter with a proximal end and a distal end, said distal end being shaped for insertion into a blood vessel along a guide wire thereby to reach remote places in the vasculature or other organs;

ii. an optical assembly positioned at the distal end of said catheter;

iii. at least one working channel running from the proximal to the distal end of said catheter;

iv. a control unit, that is not inserted into the blood vessel with the catheter, for regulating the opacity level of blood in said blood vessel around said distal end of said catheter, controllably injecting quantities of fluid into said blood vessel in the vicinity of said optical assembly, thereby enhancing visibility;

v. a local controller located at the distal end of the catheter for controlling data flow to and from an optical head at the distal end portion of the catheter, the optical head comprising an image sensor and at least one of an illumination source, a light sensor, or a shutter, and wherein the local controller is configured to control one or more functions of the optical head while coordinating signals and power with the control unit and the functions of the optical head being selected from the group consisting of (1) commanding the illumination source, (2) accepting signals from the light sensor, (3) accepting signals from the image sensor, and (4) commanding the shutter; and wherein the optical head includes a pressure sensor and the local controller receives local feedback from the pressure sensor.

10. An invasive imaging control apparatus comprising:

i. a flexible catheter with a proximal end and a distal end, said distal end being shaped for insertion into a blood vessel along a guide wire thereby to reach remote places in the vasculature or other organs;

ii. an optical assembly positioned at the distal end of said catheter;

iii. at least one working channel running from the proximal to the distal end of said catheter;

iv. a control unit, that is not inserted into the blood vessel with the catheter, for regulating the opacity level of blood in said blood vessel around said distal end of said catheter, controllably injecting quantities of fluid into said blood vessel in the vicinity of said optical assembly, thereby enhancing visibility;

v. a local controller located at the distal end of the catheter for controlling data flow to and from an optical head at the distal end portion of the catheter, the optical head comprising an image sensor and at least one of an illumination source, a light sensor, or a shutter, and wherein the local controller is configured to control one or more functions of the optical head while coordinating signals and power with the control unit and the functions of the optical head being selected from the group consisting of (1) commanding the illumination source, (2) accepting signals from the light sensor, (3) accepting signals from the image sensor, and (4) commanding the shutter; and wherein the optical head includes a light sensor and the local controller receives local feedback from the light sensor.

11. A diagnostic and operative system for use in intravascular procedures, comprising:

a flexible catheter with a proximal end and a distal end, the distal end being shaped for insertion into a blood vessel along a guide wire thereby to reach remote places in the vasculature or other organs;

a viewing apparatus positioned at the distal end of the catheter and comprising an image sensor, an optical assembly, and a light source;

at least one working channel running from the proximal to the distal end of the catheter for injecting a controlled amount of fluid into blood in the immediate region in front of the optical assembly;

an inflatable stent balloon at the distal end of the catheter; and the optical assembly located distally to the stent balloon and within a second balloon so that the injected fluid inflates the second balloon to remove red blood cells from the field of view of the viewing apparatus and to reduce the scattering of light.

* * * * *